(12) United States Patent
Parent et al.

(10) Patent No.: US 7,034,127 B2
(45) Date of Patent: Apr. 25, 2006

(54) HYDROPHILIC BIOPOLYMER-DRUG CONJUGATES, THEIR PREPARATION AND USE

(75) Inventors: Edward G. Parent, North Bergen, NJ (US); Nancy E. Larsen, Highland Mills, NY (US)

(73) Assignee: Genzyme Corporation, Cambridge, MA (US)

( * ) Notice: Subject to any disclaimer, the term of this patent is extended or adjusted under 35 U.S.C. 154(b) by 64 days.

(21) Appl. No.: 10/611,439

(22) Filed: Jul. 1, 2003

(65) Prior Publication Data

US 2004/0087488 A1  May 6, 2004

Related U.S. Application Data

(60) Provisional application No. 60/393,220, filed on Jul. 2, 2002.

(51) Int. Cl.
- *C07K 1/00* (2006.01)
- *C07K 14/00* (2006.01)
- *C07K 16/00* (2006.01)
- *C07K 17/00* (2006.01)

(52) U.S. Cl. .............. 530/402; 514/2; 514/54; 514/56; 514/57; 530/410; 525/54.1; 525/54.2; 536/21; 536/54; 536/84

(58) Field of Classification Search ............ 530/402
See application file for complete search history.

(56) References Cited

U.S. PATENT DOCUMENTS 4,582,865 A * 4/1986 Balazs et al. ............... 524/29
5,128,326 A * 7/1992 Balazs et al. ............... 514/54
5,543,332 A * 8/1996 Lihme et al. ............... 436/528
6,630,457 B1 * 10/2003 Aeschlimann et al. ........ 514/54

FOREIGN PATENT DOCUMENTS

WO  WO 93/01498  * 1/1993
WO  WO 95/13312  * 5/1995

OTHER PUBLICATIONS

Prestwich. Biomaterials from Chemically-Modifiied Hyaluronan. Feb. 26, 2001. Glycoforum. Accessed online via: http://www.glycoforum.gr.jp./science/hyaluronan/HA18/HA18.pdf on May 5, 2005.*
Lofas, S. Dextran modified self-assembled monolayer surfaces for use in biointeraction analysis with surface plasmon resonance. Pure and Appl. Chem. 1995, vol. 67, No. 5, pp. 829-834.*
Larsen et al. Hylan and Hylan Derivatives in Drug Delivery. In Cosmetic and Pharmaceutical Applications of Polymers. 1991. Edited by C.G. Gebelein et al. Plenum Press, NY. pp. 147-157.*

* cited by examiner

*Primary Examiner*—Christopher R Tate
*Assistant Examiner*—Marcela M Cordero Garcia
(74) *Attorney, Agent, or Firm*—Fish & Richardson P.C.

(57) ABSTRACT

Disclosed are methods of conjugating biologically active substances, particularly, alpha-interferon, with a hyaluronan or a mixture of a hyaluronan with at least one other hydrophilic polymer having a functional group capable of reacting with divinyl sulfone. Also disclosed are stable intermediates formed by partially reacting a hyaluronan with divinyl sulfone and stopping the reaction before completion to leave free, or reactive vinyl groups on the hyaluronan molecule available for conjugation with the biologically active substance.

3 Claims, No Drawings

HYDROPHILIC BIOPOLYMER-DRUG CONJUGATES, THEIR PREPARATION AND USE

REFERENCE TO PRIOR PROVISIONAL APPLICATION

This non-provisional application is based on and claims the benefit of the filing date (priority) of co-pending provisional application Ser. No. 60/393,220; filed Jul. 2, 2002, under 35 USC Sec. 119.

BACKGROUND OF THE INVENTION

1. Field of the Invention

The invention relates to conjugates of hydrophilic biopolymers such as hyaluronans (including hylans) with drugs or other pharmacologically active substances including anti-neoplastic drugs such as alpha-interferon formed by covalently bonding them with divinyl sulfone ("DVS"); sometimes referred to herein as vinylsulfone, methods of preparing them and using them.

2. Description of Related Art

Conjugation of polyethylene glycol ("PEG") and certain biological polymers and enzymes including insulin and catalase are disclosed in U.S. Pat. No. 4,179,337. U.S. Pat. Nos. 5,539,063 and 6,042,822 disclose respectively, (a) methods of conjugation of PEG using so-called "unique linkers" to improve the attachment and activity of the conjugates; and (b) active conjugates of alpha-interferon to PEG. U.S. Pat. No. 5,366,958 discloses the attachment of biologically active agents to fibronectin using N-hydroxysuccinimide; and International Patent No. WO 0,078,365 teaches oxidizing hyaluronans to form aldehyde groups reactive with diamines or amino polyalkylene glycols which are then reacted with oxidized sulfated polysaccharides. In U.S. Pat. Nos. 4,582,865 and 4,605,681, the preparation of cross-linked hyaluronan though vinyl sulfone linkages, as well as the attachment of these materials to the matrix of an insoluble gel-via ether linkages are described.

Prestwich, Glenn D., in "Biomaterials from Chemically-Modified Hyaluronan, Glycoforum (Mar. 29, 2001) suggests that drags way be conjugated with hyaluronan. Finally, Cirino, et al., Carbohydrate Research (1971), 17(1), 67–68) teaches that, in addition to simple cross-links (a) and simple substitutions (b), divinyl sulfone can also react with carbohydrates (e.g., cellulose, D-glucose) leading to complex modification of the carbohydrate: $RO-CH_2-CH_2-SO_2-CH_2-CH_2-OR$; and (b) $RO-CH_2-CH_2-SO_2-CH=CH_2$, wherein R is a carbohydrate.

BRIEF SUMMARY OF THE INVENTION

The invention provides methods for producing conjugates formed of a hydrophilic biopolymer such as a hyaluronan (including hylan) and a biologically active substance selected from among a large group of materials which have at least one functional group suitable for reaction with divinyl sulfone. The biologically active substance may be any substance which has biological or pharmacological activity and which is normally considered to be a drug and can thus be used as a drug component in the products according to the invention. Additionally, any such substance capable of reacting with a cross-linking agent may be the biologically active substance. The biologically active substance may, for example, be an antineoploastic agent such as vinblastin or paclitaxel, an antibiotic such as gentamicin, a protein such as α-interferon (which is also an antineoplastic agent) or Cytochrome C, an enzyme such as thrombin or a peptide such as avidin. The group of biologically active substances listed above is merely illustrative of a larger group of such substances, and is not intended to limit the scope of the invention. In fact, the biologically active substance may be any such substance having at least one chemical group reactive toward DVS. These chemical groups are typically hydroxyl, amino or sulfhydryl groups. The conjugate not only retains the biological activity of the substance, but in many instances, especially with α-interferon, exhibits enhanced, improved and/or longer lasting activity than does the un-conjugated substance, or a simple mixture of the hyaluronan and the substance.

The invention also provides the conjugates prepared by the methods of the invention.

The conjugate is the reaction product of the above-described intermediate which has the general formula $P-(O-CH_2-CH_2-SO_2-CH=CH_2)_n$, wherein n is an integer and is at least 1, P represents a hydrophilic biopolymer, and in a preferred embodiment, the biopolymer (P) is a hyaluronan or a hylan and a biologically active material capable of being covalently and nucleophilically bonded to said intermediate. The intermediate may also contain, in addition to the free, or reactive vinyl groups, some extent of DVS cross-linking.

In still a further embodiment the invention provides, in addition to the simple cross-links and substitutions described by Cirino, et al., the preparation of DVS+carbohydrate (e.g., cellulose, D-glucose, etc.) complexes of the formula: $RO-CH_2-CH_2-SO_2-CH_2-CH_2-O-(-CH_2-CH_2-SO_2-CH_2-CH_2-O-)n-CH_2-CH_2-SO_2-CH=CH_2$, wherein R is a carbohydrate and n is 0, 1, 2, 3, . . ., which complex is then reacted with R'OH, wherein R' is a drug molecule, water, a protein or an additional carbohydrate to form: $RO-CH_2-CH_2-SO_2-CH_2-CH_2-O-(-CH_2-CH_2-SO_2-CH_2-CH_2-O-)n-CH_2-CH_2-SO_2-CH_2-CH_2-OR'$, wherein n is 0, 1, 2, 3, . . . . The foregoing reaction path shows how the complex and the drug carbohydrate complex are formed. The advantage of this kind of modification is that the drug is conjugated to the carbohydrate carrier with a longer linking arm, as a result of which, the intermediate may be mare reactive to conjugating a drug.

The invention further provides pharmaceutical compositions comprising a therapeutically effective amount of the conjugate in a pharmacologically acceptable carrier or vehicle therefor.

The invention additionally provides methods of using the pharmaceutical compositions comprising the conjugates in treating neoplastic conditions comprising administering a therapeutically effective amount of the pharmaceutical composition to an animal afflicted with a neoplastic condition.

The invention still further provides methods for preparing a stable intermediate which is suitable for conjugation with drugs. The stable intermediate is prepared by reacting a hyaluronan with divinyl sulfone under controlled pH, time and temperature conditions so selected as to permit the reaction between the hyaluronan and DVS to proceed and thereafter be stopped before completion so as to leave free, or unreacted vinyl groups thereon, which are available to react with the biologically active substance to produce the conjugate.

Finally, the invention also provides the intermediate per se.

The intermediate has the general formula $P-(O-CH_2-CH_2-SO_2-CH=CH_2)_n$, wherein n is an integer and is at least 1, P represents a hydrophilic biopolymer having a functional groups capable of reacting with divinyl sulfone.

As used herein, the term hydrophilic biopolymer is intended to cover hyaluronans, hylans, or a mixture of a hylan and a hyaluronan or derivatives thereof having a molecular weight of $1 \times 10^3$ to $1 \times 10^7$ Da with at least one other hydrophilic polymer having a functional group capable of reacting with divinyl sulfone; said other hydrophilic polymer being a natural or synthetic polyanionic polysaccharide selected from among hydroxyethyl cellulose, carboxymethyl cellulose, xanthan gum, chondroitin sulfate and heparin, a protein selected from collagen, elastin, albumin, a globulin, keratin sulfate, a sulfated aminoglycosaminoglycan or a synthetic water soluble polymer.

DETAILED DESCRIPTION OF THE INVENTION

Recently, the conjugation of various biologically active materials to certain polymers has become of significant medical interest. Such conjugated materials have been found to exhibit an increase in circulatory residence time, enhanced or increased drug stability and also the ability to target specific locations for the drugs to work most effectively.

In achieving the present invention we have prepared, inter alia, conjugates of the anti-viral, anti-cancer drug α-interferon covalently attached to hyaluronan using divinyl sulfone (DVS) as a linker. Subsequent investigation of the resulting conjugates shows that the α-interferon maintains its biological activity after being coupled, or conjugated to a hyaluronan or hylan ("hereinafter sometimes referred to as "HA"). We have also demonstrated the ability of hyaluronan to bind CD44 receptors, thereby providing a targeting mechanism.

In achieving the present invention, the following experimental methods were used:

The preparation of cross-linked hyaluronan through vinyl sulfone linkages is known; see patents cited above. The reaction requires an elevated pH, typically, 9 or higher to convert the hydroxyl groups of the hydrophilic biopolymer to alkoxide ions and allow rapid reaction with the vinyl groups. The rate of the reaction is known to be dependent on pH and temperature. A rate-controlled process for effecting this was developed and is described below.

The Preparation of the Stable Intermediate

Rooster comb hyaluronan (MW 100,000 Da) was reacted with DVS while controlling the reaction rate via pH adjustment, starting at a pH of about 9.6. The reaction was stopped after 30 minutes by adjusting the pH to 6.5 with HCl. This leaves any unreacted vinyl groups covalently attached to the HA backbone, creating an "activated HA," which is the intermediate of the present invention. The unreacted DVS and hydrolysis products were removed by exhaustive dialysis. The presence of free, or reactive vinyl groups on the HA was determined by thiosulfate consumption, (J. Org. Chem., 11 (46) 719) which liberates an equivalent amount of OH into solution. By measuring pH changes in the thiosulfate with activated HA, the presence and amount of vinyl groups on the HA can be measured. The product of the reaction at this stage is a stable, reactive intermediate which can be isolated as such and then used to conjugate to a biologically active substance.

The Preparation of an Alpha-interferon+HA Conjugate

Alpha-interferon in 0.1 M carbonate buffer, pH 9.8, was added to the activated HA sample and reacted overnight in the cold. Exhaustive dialysis in 50,000 M.W. cutoff was used to eliminate excess interferon not coupled to the HA.

Samples were analyzed to determine the biological activity using an in vitro assay on a bovine kidney epithelial cell line sensitive to alpha-interferon.

Cell Adhesion

Falcon cell tissue culture plates with removable wells were coated with 1 mg per ml of hyaluronan in saline and allowed to dry overnight. Mouse melanoma cells (B16-F10) were cultured in EMEM, a commercially available tissue culture medium, with 5% fetal bovine serum. Confluent cells were dislodged with 5% EDTA, suspended in serum free medium, and labeled with Chromium-51. The $^{51}$Cr-labeled cells were plated at 40,000 cells per well for 30 minutes at 37° C. One group of cells was also incubated in the presence of anti-mouse CD44 monoclonal antibody prior to being plated. The wells were washed with PBS (phosphate buffered saline) to remove unattached cells. The entire well was then placed in a gamma counter where the radioactivity was measured to determine cell number.

Results

To determine the biological integrity of the coupled interferon, the samples were tested. The activity of the hylaluronan+alpha-interferon conjugate, sometimes hereinafter ("HA-INF conjugate") was conserved, maintaining the drug's activity after chemical modification. There was only a modest change in activity after treatment. See Table 1. To verify that HA did not interfere with the biological assay, HA was tested in the presence of interferon, and HA alone. There was no significant change in interferon activity noted in the presence of HA. HA alone had no detectable activity. It can therefore be concluded that the presence of HA does not interfere with the biological assay.

TABLE 1

Measured Interferon Activities

| Sample | Antiviral Activity |
| --- | --- |
| HA Interferon conjugate | 1.68 × 10 u/ml |
| Interferon | 2.38 × 10 u/ml |
| Interferon + HA | 2.76 × 10 u/ml |
| HA | Below Detectable Limit |

In order for the conjugate to target cells, a specific binding must be established. To investigate this aspect of the invention, we studied the binding of B16-F10 mouse melanoma cells with HA. Mouse melanoma cells over-express CD44 providing a good model for HA targeting of CD44 receptors. In the melanoma cell assay, significant binding of cells to the HA coated plates was detected, with an appreciable decrease in binding of cells that were incubated with anti-CD44 antibody prior to being plated. See Table 2. The results imply that CD44 receptors are involved in the interactions between HA and the cell. These data suggest that CD44 receptors facilitate the targeting of HA conjugated anti-cancer agents to specific cells.

TABLE 2

Cell binding to HA coated Plates

| Sample | % Binding |
| --- | --- |
| Coated 1.0 mg/ml HA | 35.0% |
| Coated + Anti CD44 Antibody | 11.8% |

The present invention is described in more detail in the following examples, which are given merely by way of illustration and are not intended to limit the invention as set forth in the claims. Unless otherwise indicated, all concentrations given are by weight. The hyaluronan used in the following examples was rooster comb hyaluronan (MW 100,000 Da) which is described in the prior art

EXAMPLE 1

0.05 gram of hyaluronan was dissolved in 10 ml of sterile water. The final concentration was 5 mg per ml. After 2 days of mixing, the sample was autoclaved for 30 minutes at 121° C. to reduce the molecular weight of the sample. The sample was subsequently diluted with 10.0 ml of 0.5M carbonate buffer at pH 9.6, after which 5.0 µg of vinyl sulfone were added to the solution followed by vigorous mixing. The sample was placed on a shaker at 4° C. for 30 minutes. The pH was adjusted to 6.5 by the addition of HCl. The sample was then placed in dialysis against 2 liters of 0.1M phosphate buffer pH 6.5 followed by dialysis against 800 volumes of water.

EXAMPLE 2

0.05 gram of hyaluronan was dissolved in 10 ml of sterile water. The final concentration was 5 mg per ml. After 2 days of mixing, the sample was autoclaved for 30 minutes at 121° C. to reduce the molecular weight of the sample. The sample was subsequently diluted with 10.0 ml of 0.5M carbonate buffer at pH 9.6, after which 5.0 µg of vinyl sulfone were added to the solution followed by vigorous mixing. The sample was placed on a shaker at room temperature, i.e., about 20° C. for 30 minutes. The pH was adjusted to 6.5 by the addition of HCl. The sample was then placed in dialysis against 2 liters of 0.1M phosphate buffer pH 6.5 followed by dialysis against 800 volumes of water.

EXAMPLE 3

Alpha-interferon (500,000 units) in 1 ml of 0.1M carbonate buffer, pH 9.9, were mixed with 2 ml of the sample from Example 1. The mixture was placed on a shaker for 24 hours in the cold and dialyzed against 10,000 volumes of saline solution. Samples were tested for biological activity in an assay using interferon sensitive bovine kidney epithelial cells. The biological activity of the composition was 230,064 units per ml.

EXAMPLE 4

Alpha-interferon (500,000 units) in 1 ml of 0.1M carbonate buffer, pH 9.9, were mixed with 2 ml of the sample from Example 2. The mixture was placed on a shaker for 24 hours in the cold and dialyzed against 10,000 volumes of saline solution. Samples were tested for biological activity in an assay using interferon sensitive bovine kidney epithelial cells. The biological activity of the composition was 167,000 units per ml.

EXAMPLE 5

0.5 gram of hyaluronan was dissolved in 100 ml of sterile water. The final concentration was 5 mg per ml. After 2 days of mixing, the sample was autoclaved for 20 minutes at 121° C. to reduce the molecular weight of the sample. 15 ml of the solution were subsequently diluted with 15.0 ml of 0.5M carbonate buffer at pH 9.6.5 after which 5.0 µg of divinyl sulfone were added to the solution followed by vigorous mixing. The sample was placed on a shaker at room temperature for 30 minutes. The sample was then neutralized by adding 4.9 ml of 0.5M sodium phosphate monobasic to the solution. The sample was adjusted with HCl to pH 6 and placed into sterile dialysis tubing and dialyzed against 500 volumes of water.

EXAMPLE 6

Alpha-interferon (four million units) were reconstituted in 1 ml of 0.5 M carbonate buffer, pH 9.9. One ml of the interferon solution was added to 3 ml of the composition prepared in Example 5, then placed in the cold for 24 hours. The sample was then dialyzed against 500 volumes of saline in the cold for 18 hours. Samples were tested for biological activity in an assay using human pancreatic carcinoma cells. The biological activity of the composition was 1,620,247 units per ml.

EXAMPLE 7

0.25 gram of hyaluronan was dissolved in 50 ml of sterile water. The final concentration was 5 mg per ml. After 2 days of mixing, the sample was autoclaved for 45 minutes at 121° C. to reduce the molecular weight of the sample. The sample was subsequently diluted with 50 ml of 0.5M carbonate buffer at pH 9.6, after which 10.0 µl of vinyl sulfone were added to the solution followed by vigorous mixing. The samples were placed on a shaker at 4° C. for 30 minutes. The pH was adjusted to 6.5 by the addition of HCl. The sample was then placed in dialysis against 2 liters of 0.1M phosphate buffer pH 6.5 followed by 8 changes of 2 liters of water.

EXAMPLE 8

200 µl of epidermal growth factor were brought to a final volume of 1.0 ml in 0.1M carbonate buffer, pH 9.6, and mixed with 1 ml of the activated hyaluronan from Example 7. The mixture was placed on a shaker for 24 hours in the cold and dialyzed against 1,000 volumes of saline. An increase in the molecular weight profile of the HA was observed using HPLC. An absorbance at 280 nm indicated the presence of protein that was not separated by HPLC.

EXAMPLE 9

0.2 mg of Rhodamine labeled Avidin in 1.0 ml of 0.1M carbonate buffer, pH 9.6, was mixed with 1 ml of the activated hyaluronan from Example 7. The mixture was placed on a shaker for 24 hours in the cold and dialyzed against 1,000 volumes of saline. After exhaustive dialysis, a strong fluorescent signal was observed indicating the presence of Avidin that could not be separated by HPLC.

EXAMPLE 10

20 μg of Paclitaxel in 0.20 ml were brought to a final volume of 1.0 ml in 0.1M carbonate buffer, pH 9.6 and mixed with 1 ml of activated hyaluronan from Example 7. The mixture was placed on a shaker for 24 hours in the cold and dialyzed against 1,000 volumes of saline. 100 μl of the resulting conjugate in 1 ml of media were incubated with human hepatoma cells for 24 hours causing a 53% reduction in cell growth.

EXAMPLE 11

0.2 ml of Anti-BSA Antibody was brought to a final volume of 1.0 ml in 0.1M carbonate buffer, pH 9.6, and mixed with 1 ml of the activated hyaluronan from Example 7. The mixture was placed on a shaker for 24 hours in the cold and dialyzed against 1,000 volumes of saline. An increase in the molecular weight profile of the HA was observed using HPLC. An absorbance at 280 nm indicated the presence of protein that was not separated by HPLC.

EXAMPLE 12

200 μg of Cytochrome C were dissolved in 1.0 ml of 0.1M carbonate buffer, pH 9.6, and mixed with 1 ml of the activated hyaluronan from Example 7. The mixture was placed on a shaker for 24 hours in the cold and dialyzed against 1,000 volumes of saline. An increase in the molecular weight profile of the HA was observed using HPLC. An absorbance at 280 nm indicated the presence of protein that was not separated by HPLC.

EXAMPLE 13

25 μg of Vinblastin were dissolved in 1.0 ml of 0.1M carbonate buffer, pH 9.6, and mixed with 1 ml of the activated hyaluronan from Example 7. The mixture was placed on a shaker for 24 hours in the cold and dialyzed against 1,000 volumes of saline. 100 μl of the conjugate in 1 ml of media were incubated with human hepatoma cells for 4 hours causing a 34% hepatoma cell death.

The invention claimed is:

1. A conjugate comprising a reaction product of an intermediate having the formula P—(O—$CH_2$—$CH_2$—$SO_2$—CH=$CH_2$)$_n$, wherein n is an integer and is at least 1, and P represents a hydrophilic biopolymer, with a biologically active material capable of being covalently bonded to said intermediate, wherein the hydrophilic biopolymer is hyaluronan and the biologically active material is alpha-interferon.

2. A conjugate according to claim 1, having the formula HA-O—$CH_2$—$CH_2$—$SO_2$—$CH_2$—$CH_2$—NH—INF, wherein HA represents a hyaluronan moiety and INF represents an alpha-interferon moiety.

3. A conjugate according to claim 1, wherein the hyaluronan has a molecular weight of about $1\times10^3$ to $1\times10^7$ Da.

* * * * *